United States Patent [19]

Couchman

[11] 4,142,154

[45] Feb. 27, 1979

[54] HOLE TESTER USING A PERMEABLE PROTECTIVE SLEEVE INSERTIBLE IN SAID HOLE AND ADAPTED TO RECEIVE A RELATIVELY MOVABLE EDDY CURRENT PROBE

[75] Inventor: James C. Couchman, Fort Worth, Tex.

[73] Assignee: General Dynamics Corporation, Fort Worth, Tex.

[21] Appl. No.: 833,942

[22] Filed: Sep. 16, 1977

[51] Int. Cl.² ............................................. G01R 33/12
[52] U.S. Cl. ..................................... 324/219; 324/238
[58] Field of Search ................................ 324/219–221, 324/226, 228, 234, 236, 237, 238, 225, 261, 262

[56] References Cited

U.S. PATENT DOCUMENTS

| 2,540,588 | 2/1951 | Long | 324/219 |
|---|---|---|---|
| 2,955,253 | 10/1960 | Bryant et al. | 324/220 |
| 3,209,243 | 9/1965 | Walters et al. | 324/220 |
| 3,718,855 | 2/1973 | Rogel et al. | 324/219 |
| 3,831,084 | 8/1974 | Scalese et al. | 324/219 |

OTHER PUBLICATIONS

Reeves, C. R., A Mechanized E. C. Scanning System for Aircraft Struts; Mat. Eval.; Mar. 1973; pp. 48–52.

*Primary Examiner*—Robert J. Corcoran
*Attorney, Agent, or Firm*—Charles E. Schurman

[57] ABSTRACT

Inspection for hole quality in structures is enhanced by inserting a smooth, thin-wall hollow sleeve into a hole to be tested and moving an eddy current probe within the sleeve. Mechanization is improved by apparatus which inserts and holds the sleeve in the hole and has drive means operable so as independently to rotate the probe or move it linearly, or both, within the stationary sleeve.

25 Claims, 6 Drawing Figures

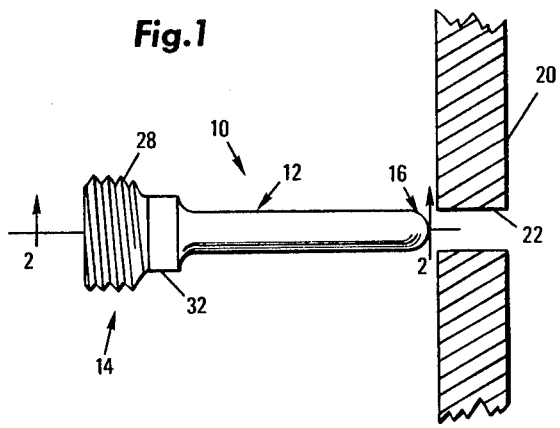
Fig.1
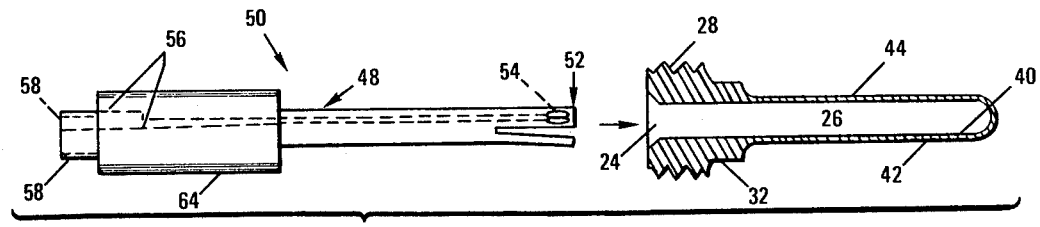
Fig.2
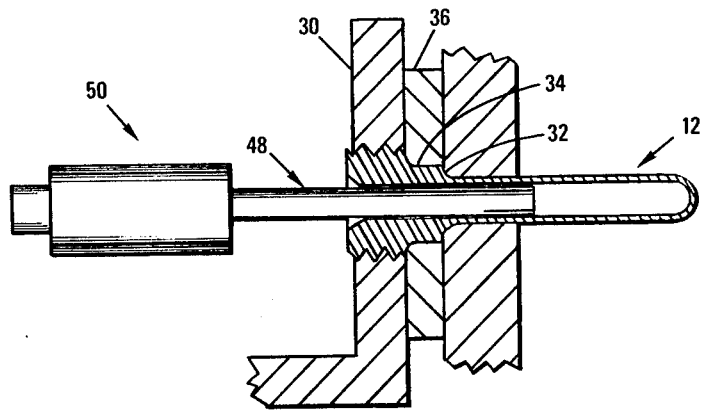
Fig.3
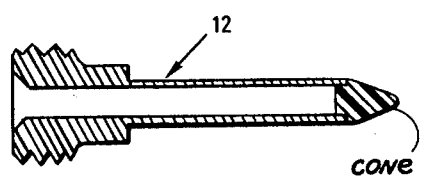
Fig.4 cone
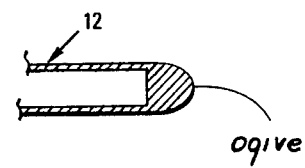
Fig.5 ogive

HOLE TESTER USING A PERMEABLE PROTECTIVE SLEEVE INSERTIBLE IN SAID HOLE AND ADAPTED TO RECEIVE A RELATIVELY MOVABLE EDDY CURRENT PROBE

BACKGROUND OF THE INVENTION

Quality assurance standards particularly in critical areas of aerospace construction such as aircraft and space vehicles have become increasingly stringent as the need to improve the predictable life and performance of such structures has increased. Holes formed in metal structures to receive fastener devices such as rivets, bolts or special fasteners are subject, particularly under the pressures of mass production, to the presence of flaws such as burrs, scratches, gouges, out-of-roundness, and others. Holes may also be formed at or near the presence of slight imperfections in the metal which can affect hole quality. If undetected, such flaws can seriously impair the mission life of a given structure by resulting in premature failure due to fatigue or other cracking at the fastener hole.

One previous method of inspection for flaws in or at fastener holes has been the use of eddy current detection. In this method a small energized electrical coil is passed over the interior surface of the hole thereby inducing eddy currents in the surrounding metal. Presence of flaws or aberrations is ascertained by detecting changes in current flow in the coil circuit resulting from its altered effective inductance when the character of the metal structure changes, for example, if a cut or gouge is present. Conventionally, the coil is incorporated into the tip of a small rod-like probe which is passed into the hole manually or by mechanical means. Manual use, however, is slow and subject to erroneous readings due to uneven and unsteady insertion. In the prevalent previous mechanized method the probe is inserted by mechanical means directly into the hole where it is held by spring action against the hole inner surface and moved only in a predetermined helical pattern, e.g., by constant linear advance with a constant rate of rotation. In these uses, however, it has been found that scratches and other flaws in the hole inner surface can scar and abrade the material of the probe which is typically a resinous plastic material. When this occurs, then even over a short period of repeated use the probe tip may be so worn as to cause shorting out of the probe coil thus destroying usefulness of the probe and requiring its replacement. Moreover, with conventional eddy current probes detection sensitivity is highly affected by lift-off frequency settings. "Lift-off" frequency is that electrical frequency to which the probe coil circuit is adjusted to minimize the "noise" which occurs when the probe just separates or lifts off the surface of the material being tested. In prior art use of a probe inserted directly into the hole, the probe tip may at times insufficiently contact the hole inner surface. This results in undesirable lift-off "noise" signals which tend to obscure the electrical signatures of flaws. While normally the circuit driving frequency is tuned for minimal reaction to surface lift-off, in practice the circuit often becomes slightly detuned with resulting increase in noise leading to signal misinterpretation or missed flaws and the necessity of repeated tuning. Non-axially aligned probe insertion may also contribute to noise and spurious signals.

Other drawbacks to prior eddy current inspection of holes include its being generally insensitive to detecting out-of-round holes and the heretofore limited mechanized modes of probe movement which are inadequate for the precision computer control of the inspection process contemplated herein. As a result of these factors, use of eddy current inspection has been restricted to less than its potential.

SUMMARY OF THE INVENTION

The present invention does much to overcome the indicated difficulties of the prior art and provides improved devices, method and apparatus whereby eddy current inspection may be more certainly and economically carried out. Consequently the quality and effectiveness of this type of hole inspection, particularly for fastener holes, in metal structures is substantially enhanced.

It has been determined in accordance with the invention that when a smooth intermediary or reference surface of durable but electromagnetically permeable material, e.g., materials having a higher electromagnetic field penetration depth than that of the metal adjacent the hole to be inspected, is positioned between the eddy current probe and the inner wall of the hole, probe wear is drastically reduced, sensitivity to lift-off frequencies is reduced or eliminated and sensitivity to out-of-roundness is greatly increased. This construction makes the eddy current inspection process less costly, more reliable and of increased utility. The intermediary surface provides a known or reference smoothness, e.g., one producing no or minimal noise by substantially eliminating lift-off and which does not abrade or wear, to any significant degree, the material of the probe. Moreover, by providing for mechanical holding of the reference material in place and independently controllable linear and rotational movement of the probe it is feasible to employ computer control of the inspection process so that flaw signatures can be more readily and accurately determined due to lessened interference from extraneous or unwanted signals even when the eddy current coil circuit becomes detuned with respect to a particular hole and material.

Accordingly, this invention contemplates a thin-walled hollow sleeve device smooth on its inner and outer walls and open at least at one of its ends for receiving closely fitted therein an eddy current probe for linear and rotational movement within and with respect to the sleeve interior. Each such sleeve is sized to substantially true roundness in and out and to fit closely within a given size hole to be tested. Advantageously the sleeves are formed from a material that combines rigidity and durability with the characteristic of being electromagnetically permeable so as to permit electromagnetic field penetration through the sleeve and into the material being inspected to the requisite inspection depth. Beneficially, such sleeve material has an electromagnetic field penetration depth equal to or greater than that of the material to be inspected. Beneficially, the sleeve device may incorporate aligning means at its base or proximal end aligned to the axis of the sleeve for assuring proper insertion of the sleeve in the hole and connector means to attach the device to supporting and positioning structure.

Structural metallic materials commonly used in the aerospace field, for example, and which may require inspection of hole quality are likely to be aluminum, nickel, ferrous metals and titanium. For the improved inspection of these materials it has been found that metallic compositions containing a high percentage of titanium, i.e., at least about 70% titanium, combine excellent durability and strength characteristics, good machinability and may be polished to the requisite degree. They are thus able to provide sufficient rigidity in thin walled structures while allowing good penetrability of the eddy current inducing field through the titanium composition and into the adjacent structure being tested. As an indication of this, titanium in its elemental form is found to have an electromagnetic field penetration depth significantly exceeding molybdenum, aluminum, nickel, iron and the steels at all probe coil driving frequencies from $10^1$ to about $10^8$ Hertz. Durability may be defined as high resistance to wear over repeated insertion and withdrawals of a sleeve into and from holes formed in the materials stated above.

Excellent results have been obtained using a composition nominally containing 6% aluminum, 4% vanadium and the balance titanium except for minor amounts of up to about 1% residuals and impurities. Other suitable compositions are a nominal 8% aluminum, 1% molybdenum, 1% vanadium, and the balance titanium with residuals and impurities as aforesaid. Yet another suitable titanium composition contains nominally about 11.5% molybdenum, 6% zirconium, 4.5% tin with the balance titanium and the above stated minor amounts of other materials. The 6Al-4V-Ti alloy is preferred.

While the titanium sleeves are found especially advantageous for the inspection of aluminum materials, sleeves in accordance herewith may also be formed using materials other than titanium, for example, of certain nickel alloy compositions, where their electromagnetic field penetration depth would exceed that of certain steels to be inspected that have lesser penetration depths. The sleeves formed in accordance herewith may be hand inserted into the hole being tested and held secured in place manually or by other means and the eddy current probe likewise manually inserted and moved in the sleeve. Improved results, however, are obtained using the sleeve with the herein disclosed mechanical equipment or apparatus. Accordingly, suitable apparatus has been found to include a support means having the hollow sleeve device extended therefrom for mechanically inserting the sleeve into a hole having mounted thereon means for independently moving the eddy current probe either linearly or rotationally or both at variable speeds within the hollow sleeve by selectable amounts and at variable speeds. This versatility of action improves the ability to locate flaws and to re-examine areas passed over by the eddy current coil. It also provides for computerized mechanization and analysis of the inspection process including mechanically positioning the support means to place the sleeve and probe over the hole to be tested, pushing the support to effect sleeve insertion followed by passing the energized probe tip or coil over the inner surface of the sleeve and hole as above and measuring the resulting probe inductance.

Thus, one object of the invention is to provide the use of a thin walled titanium-containing sleeve that is polished inside and out and machined to a snug fit into a fastener hole, is rigid and will not be or is highly resistant to being scratched or mis-shaped by the fastener holes in aluminum or other materials that are being inspected nor will it change the hole quality.

Another object of this invention is to provide means and methods for use by which the eddy current probe will have a very long wear life within the polished interior of the titanium sleeve device and will largely eliminate the probe wear-out problem that hinders routine production line use of conventional eddy current probes.

Yet another object is to provide a thin, uniform sleeve which through being substantially round and of known inside surface smoothness makes an eddy current probe fitted closely therein substantially insensitive to producing false indications as to hole quality which heretofore resulted from de-tuning or drifts in lift-off frequency.

BRIEF DESCRIPTION OF THE DRAWINGS

The above and further objects and advantages of the inventive concepts herein will become more apparent by attention to the annexed drawings, description of preferred embodiments and discussion, given by way of example only and not as limitative thereof and in which:

FIG. 1 is a plan view of a sleeve device of this invention showing the sleeve positioned to be inserted into a hole to be tested or inspected;

FIG. 2 is a compound figure including a cross-sectional view of the sleeve device of FIG. 1 taken along line 2—2 also showing an eddy current probe positioned to be inserted into the sleeve;

FIG. 3 is a sectional view showing the sleeve device held in a support structure and inserted into a hole to be tested and an eddy current probe inserted into the sleeve device;

FIG. 4 is a cross-sectional view of another embodiment of the sleeve device of FIG. 1 showing a mushroom cap forming the tip of the sleeve; and FIG. 5 is a partial view in cross-section of the distal end or tip of a sleeve device having an ogive configuration, which is the preferred embodiment.

DESCRIPTION OF THE PREFERRED EMBODIMENTS

Figure 6:
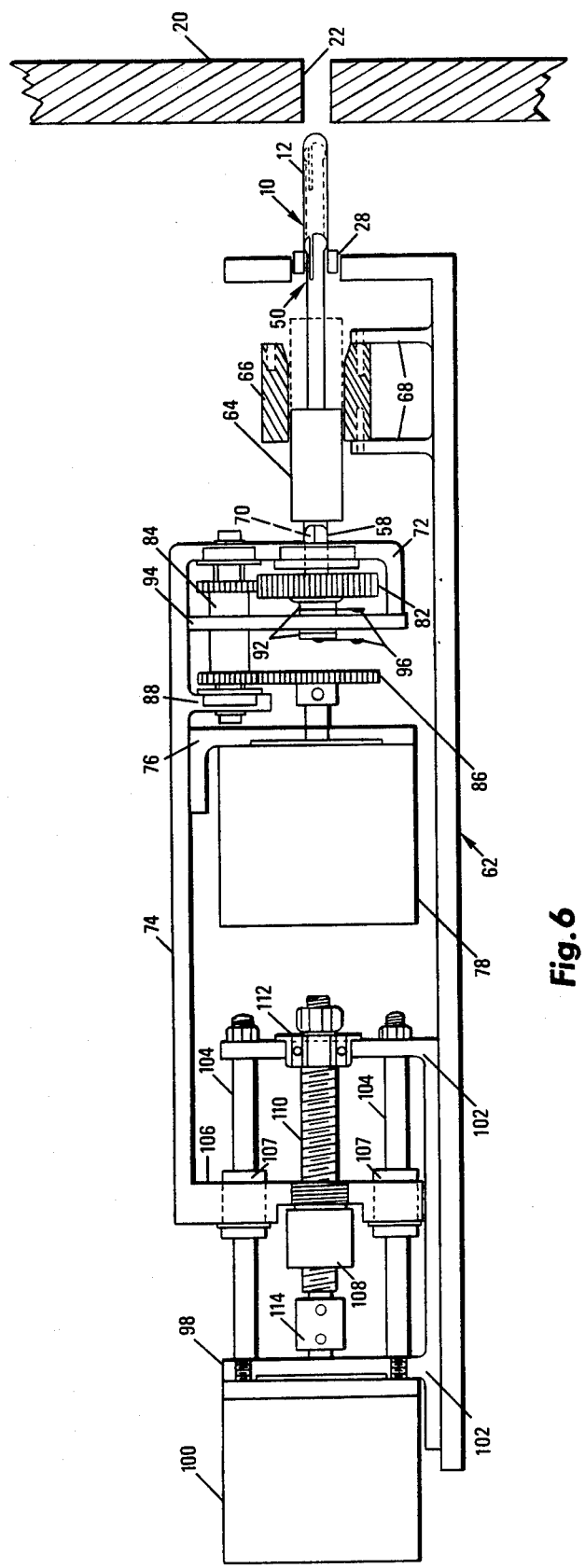
FIG. 6 is an elevational view of apparatus of the invention for inserting and holding the sleeve in a hole to be inspected and for moving an eddy current probe within the inserted sleeve in the hole.

Referring to the drawings, an eddy current inspection or sleeve device 10 of this invention has a relatively narrow hollow cylindrical sleeve portion or sleeve 12 joined to and extending from a relatively larger base portion 14. The sleeve terminates at the distal end of the device in a tip 16 rounded so as to avoid marring or scratching the entrance or bore of a hole 20 formed in a structure 22 when the sleeve is inserted in the hole to test or inspect the quality of the metal of surrounding the hole. At its proximal end the sleeve device has a chamfered opening 24 through the base portion communicating with a hollow interior 26 extending substantially the full length of the device including the sleeve. Sleeve device 10 is also threaded externally at its base portion which provides a connecting means 28 for attaching the device to mating threads in a support mean 30. Between the threads and the sleeve the base portion 14 incorporates a cylindrical thimble 32 of greater diameter than the sleeve which can be engaged into a matching alignment recess 34 in the hole drilling template 36 used to drill the hole 20.

Sleeve device 10 has its entire interior surface 40 formed concentrically with sleeve exterior surface 42 and the thimble 32 thus providing the sleeve 12 as a uniform thickness, tubular sleeve wall 44 in axial concentricity with the thimble. Wall 44 is machined and polished to a thickness of 0.010 inches with an optimum variation in thickness only from about 0 to about 1 mil. Inside and outside surfaces 40 and 42 both are polished to a root mean square smoothness of as close to 1 micro inch as possible but up to a maximum of about 5 micro inches r.m.s. will give satisfactory results. For any given size of hole to be inspected, sleeve 12 is sized to be from between about 0.002 inch to about 0.005 inch less than the inside dimension of the hole. The sleeve is also sized to be substantially exactly round in cross section throughout its length. However, good results can be achieved if the sleeve is formed to have a tolerance difference between minimum and maximum diameters of its outer surface of a maximum of about 0.003 inches. With this construction any misfit between the sleeve and an out-of-round fastener hole makes out-of-roundness flaws more detectable than in the case where a sleeve is not used since the eddy current technique can reveal the slight space between the sleeve and the hole occasioned by out-of-roundness.

As will be apparent from the drawings the interior 26 of device 10 is adapted to receive therein through opening 24 a probe rod portion 48 of a conventional eddy current probe 50 having embedded in the probe tip 52 an eddy current inducing coil 54 connected by leads 56 to the usual socket contacts 58. Such probes are available commercially in various sizes to order. Thus, probes are used that have a rod portion which makes snug slidable fit at the tip (i.e., at the coil location) against the interior surface 40. For this purpose the probe tip (typically) is split and slightly spread at 60 which provides the necessary spring action to engage the bore.

Referring to FIG. 6 showing apparatus for mechanized and computerized operation of eddy current hole inspection it can be seen that a sleeve device 10 is attached by connecting means 28 to a support means 62 of the apparatus. Also supported on the apparatus from support means 62 is an eddy current probe 50 positioned to have its tip end maintained inserted into the open end of the sleeve device. The barrel 64 portion of the probe at the end opposite the probe tip is guided in probe guide 66 having its bore aligned with the bore of the sleeve and supported from the support means by uprights 68. The base end of the probe removably connects by its socket contacts 58 to a hub 70 rotatable in a first extension piece 72 joined to a bracket 74. The bracket supports, via arm 76, a drive motor or means 78 for imparting rotational movement to the eddy current probe. Hub 70 is operatively connected at its rearward end to drive motor 78 via gear 82 to an axle 84 having connecting gears at its opposite ends the rearmost of which is driven by drive gear 86. The axle is suspended at its forward end from first extension piece 72 and at its rearward end at a second extension piece 88 also extending from bracket 74.

Provision for electrical connection to the probe coil is made by a pair of slip rings 92 journalled in a spider 94 and making electrical contact with hub 70 through the center portion of gear 82. Electrical leads (not shown) connect to the slip rings' contacts 96 to supply excitation current through hub 70 socket contacts 58 to the eddy current probe coil from a source not shown. These leads connect to known electrical inductance detection means (not shown) for detecting and measuring changes therein as the probe is moved in the sleeve within the hole.

Also carried on the support means 62 is a frame 98 to which is attached drive means or motor 100 for imparting linear drive or movement to the eddy current probe. For this purpose frame 98 has a pair of slide rods 104 connecting between forward and rearward frame arms 102. A cross arm 106 extending from bracket 74 carries a pair of sliders 107 freely slidable on the slide rods 104. The cross arm carries a cross head 108 interiorly threaded to move along threaded travel screw 110. The travel screw is turnable in a bearing 112 in the forward frame arm and is secured at its other end to the motor 100 output shaft by connector 114, which provides for linear travel of the cross head, bracket 74 and the probe 50.

Each of the drive means is an electric synchronous stepping motor that when energized is controlable (from source not shown) to impart variable speed reversible rotary movement to its output shaft. The apparatus may thus be held movably and operated or attached to a mechanized holder and operator (neither shown) such as a computer controlled robot to position the sleeve over a hole to be inspected and to push the sleeve into the hole. Thereafter, either or both drive means can be operated to move the probe linearly or rotationally, or both, by selected amounts at variable speeds either forward or in reverse.

The sleeves of this invention should have a wall thickness sufficient to support a mechanical load of inserting the sleeve into the hole but be as thin as possible for transmitting the maximum amount of electromagnetic energy. That is, they should permit a maximum electromagnetic field penetration or skin depth into the material being inspected so as to induce maximum eddy currents therein thereby maximumizing sensitivity.

It will be appreciated that the sleeves provided for herein provide an intermediary material between an eddy current probe and the surface being inspected which both acts as a window to an electromagnetic field and provide a smooth slide for engaging the probe tip which has a known smoothness thus acting as a reference standard for judging and comparing the signals received in the probe circuit thus facilitating pattern recognition of differing flaw signatures which may be digitized and detected through computer analysis.

The socket-like sleeves taught herein may vary in wall thickness, depending on the use involved from between about 0.005 inch to about 0.100 inch subject to the above stated requirements for maximum transmission therethrough of an electromagnetic field. Also, the support means 30 may be a closed cylinder surrounding the apparatus with the sleeve actually aligned at one end thereof with the axis of the cylinder to facilitate attachment to a robot by bolts or the like.

Various modifications may be made by those skilled in the art without departing from the spirit and scope of the invention.

What is claimed is:
1. A sleeve device forming a reference surface of generally known smoothness and thickness at the interiors of holes to be tested for improving eddy current inspection of hole quality in structures comprising:
 a durable, substantially rigid, thin wall hollow sleeve open at least at one end for receiving an eddy current probe for sliding movement therein during hole testing,
 said sleeve being cylindrical along its length and adapted to be inserted into a hole to be tested inde- pendently of an eddy current probe and sized to fit closely within said hole, the sleeve wall being of substantially uniform thickness along its length and its inside and outside surfaces being polished to substantially known smoothness to avoid marring of an eddy current probe moved therein or marring of the interior of the hole to be inspected, and to substantially eliminate lift-off like noise signals from the probe due to hole surface roughness, the sleeve being formed from an electromagnetically permeable material which permits electromagnetic field penetration through the sleeve wall to the desired depth in the material to be inspected.

2. The sleeve device of claim 1 in which said electromagnetically permeable material has an electromagnetic field penetration depth equal to or greater than that of the material to be inspected.

3. The sleeve device of claim 1 in which said electromagnetically permeable material is a metal alloy containing not less than about 70% titanium.

4. The sleeve device of claim 3 in which said metal alloy is a composition containing about 89% Ti, about 6% Al and about 4% V, the balance being residuals and trace elements.

5. The sleeve device of claim 1 in which the sleeve is substantially concentrically round inside and out.

6. The sleeve device of claim 5 in which the difference between the minimum and maximum diameter of the sleeve outer surface has a maximum variation of about 0.003 inch.

7. The device of claim 1 in which said sleeve is of substantially constant diameter inside and outside for a substantial portion of its length.

8. The sleeve device of claim 1 in which means are provided at the sleeve distal end to avoid marring of a hole interior.

9. The device of claim 1 in which the distal end is closed.

10. The device of claim 9 in which said closed distal end forms a curved figure of revolution.

11. The device of claim 10 in which said figure of revolution is ogive-like.

12. The device of claim 8 in which said distal end is cone-like.

13. The device of claim 1 in which the proximal end thereof has connecting means for holding said sleeve fixed to a support structure to permit an eddy current probe to be moved within said sleeve.

14. The sleeve device of claim 1 in which the exterior dimension of the sleeve is from about 0.002 inch to about 0.005 inch less than the inside dimension of the hole to be inspected.

15. The sleeve device of claim 7 in which said sleeve wall varies in thickness along said substantially constant diameter portion only from about 0 to about 1 mil.

16. The sleeve device of claim 1 in which said smooth inside and outside surfaces are polished to a root mean square smoothness of between about 1 to about 5 micro inches.

17. The sleeve device of claim 1 in which the wall thickness is from about 0.005 inch to about 0.100 inch.

18. The sleeve device of claim 1 in which said device has means for axially aligning said sleeve with the axis of a hole to be inspected to provide proper alignment of the sleeve in the hole.

19. Apparatus for conducting eddy current inspection of hole quality in metal structures comprising:

support means movable towards or away from a hole to be inspected by eddy current probe testing;

a sleeve device carried by said support means and having a smooth surfaced hollow sleeve adapted to be inserted by movement of said support means into a hole in a structure to be tested and to slidably receive an eddy current probe interiorly of said sleeve upon insertion of the sleeve, an eddy current probe operatively positioned in said support means and connectable to a source of excitation and to means for probe coil inductance detection, said probe operably connected to a pair of drive devices each independently operative respectively to impart linear or rotational movement or both to said probe with respect to said hollow sleeve, and said probe and said sleeve disposed in axial alignment one to the other, whereby movement of said support means can be effected to insert said sleeve into the hole to be tested and selective operation of one or the other or both of said drive devices is effective to move said probe in said sleeve for eddy current detecting of flaws which may be present in the structure adjacent to said hole.

20. The apparatus of claim 19 in which said sleeve device has aligning means thereon for positioning the sleeve into axial alignment with the bore of the hole to be inspected.

21. The apparatus of claim 19 in which means are provided for detachably connecting the sleeve to the housing.

22. The method for eddy current inspection of hole quality in a metallic structure which comprises:

inserting into the hole to be inspected a thin wall hollow sleeve open at least at its proximal end to receive therethrough an eddy current probe, said sleeve sized to fit closely within said hole with the interior and exterior surfaces of said sleeve thin wall being smooth so as to avoid marring of said probe and the hole to be inspected, advancing into the sleeve an eddy current probe sized to fit closely within said sleeve and adapted to be rotated and moved linearly with respect to said sleeve and said hole, the probe being further adapted when energized to induce eddy currents in said structure adjacent said hole and operatively connected to an excitation source and detection means for determining changes in said eddy currents produced by flaws in said structure if present, said probe being energized for inducing eddy currents in said structure, and a detectable electrical signal therefrom, moving said probe within said sleeve with respect thereto and to said hole and said structure, and detecting electrical signals from said probe.

23. The method of claim 22 in which said probe movement is accomplished by simultaneously moving the probe linearly and rotationally.

24. The method of claim 22 in which said probe movement is accomplished by moving the same linearly without rotational movement.

25. The method of claim 22 in which said probe movement is accomplished by moving the same rotationally without linear movement.

* * * * *